(12) United States Patent
Mancini et al.

(10) Patent No.: US 10,478,349 B2
(45) Date of Patent: Nov. 19, 2019

(54) BODY FLUID SENSOR PAD

(71) Applicant: Sentine, Inc., Huntsville, AL (US)

(72) Inventors: Ralph Joseph Mancini, Danbury, CT (US); Derek Phelps Gardner, Huntsville, AL (US)

(*) Notice: Subject to any disclaimer, the term of this patent is extended or adjusted under 35 U.S.C. 154(b) by 294 days.

(21) Appl. No.: 15/330,222

(22) Filed: Aug. 26, 2016

(65) Prior Publication Data

US 2017/0112681 A1    Apr. 27, 2017

Related U.S. Application Data

(60) Provisional application No. 62/283,348, filed on Aug. 28, 2015.

(51) Int. Cl.
*A61F 13/42*     (2006.01)

(52) U.S. Cl.
CPC ........ *A61F 13/42* (2013.01); *A61F 2013/424* (2013.01)

(58) Field of Classification Search
CPC ............................ A61F 13/42; A61F 2013/424
See application file for complete search history.

(56) References Cited

U.S. PATENT DOCUMENTS

| | | | |
|---|---|---|---|
| 8,795,257 B2* | 8/2014 | Coulthard | A61F 13/02 604/541 |
| 10,022,277 B2* | 7/2018 | Heil | A61F 13/42 |
| 2006/0244614 A1* | 11/2006 | Long | A61F 13/42 340/573.5 |
| 2013/0041334 A1* | 2/2013 | Prioleau | A61F 13/42 604/361 |
| 2016/0120455 A1* | 5/2016 | Pop | A61B 5/208 600/301 |
| 2018/0049926 A1* | 2/2018 | Lin Charna | H04B 1/3888 |
| 2018/0055697 A1* | 3/2018 | Mihali | A61F 13/42 |

* cited by examiner

*Primary Examiner* — Sarah B McPartlin
(74) *Attorney, Agent, or Firm* — Lanier Ford Shaver & Payne PC; Jeremy A. Smith

(57) ABSTRACT

The present subject matter relates to absorbent articles and signaling devices for use therewith. The signaling device can be configured to detect the presence of an insult in the absorbent article and/or in an undergarment. The signaling device can be further configured to determine whether the insult is a urine insult or a feces insult. The signaling device can provide a notification to a user that an insult has occurred and can inform the user whether the insult is a urine insult or a feces insult.

9 Claims, 2 Drawing Sheets

BODY FLUID SENSOR PAD

This application claims benefit of U.S. provisional application No. 62/283,348 filed on Aug. 28, 2015.

FIELD OF THE INVENTION

The present invention relates to a signaling device configured to detect the presence of moisture in the absorbent article and/or in an undergarment. The signaling device can further wirelessly and/or visually provide notification to a nursing station and/or caregiver that an insult has occurred, thereby speeding up the response time for patient care.

BACKGROUND OF THE INVENTION

Decubitis ulcers, bed sores, and irritant diaper dematitis (IDD) occurs when continuous pressure, temperature, and body waste such as urine is in prolonged contact with skin. Deucbitis ulcers and bed sores are more frequent with the elderly or diabetic patients in home such as nursing homes or actute care facilities. IDD occurs frequently in babies due the sensitive nature of their skin. Frequent and prolonged skin contact with stool due to fecal incontinence and diarrhea are high risk factors for severe IDD. Many of these risks can be overcome by recent innovations in absorbent article technology, including absorbent articles having superabsorbent layers, reduced skin wetness, and superior pH control. The prevention of urine in contact with skin for a prolonged period, however, still poses a challenge. For instance, many absorbent articles include hydrophobic liquid permeable inner layers that permit urine to pass through the layer so that the urine does not contact the skin even after multiple insults. However, many of these absorbent articles fail to completely protect the user against prolonged contact of body waste with the skin.

Absorbent articles such as bed pads, diapers, training pants, incontinence products, feminine hygiene products, swim undergarments, and the like conventionally include a liquid permeable body-side liner, a liquid impermeable outer cover, and an absorbent core. The absorbent core is typically located in between the outer cover and the liner for taking in and retaining liquids (e.g., urine) exuded by the wearer. Various types of moisture or wetness indicators have been suggested for use with absorbent articles. These wetness indicators, however, are complicated, costly and add additional burdens to an already overloaded caregiver.

The present invention provides a simple and cost effective signaling device configured to detect the presence of moisture in a bed pad, absorbent article and/or in an undergarment. The signaling device wirelessly and/or visually provides notification to a nursing station and/or caregiver that an insult has occurred, thereby speeding up the response time for patient care. Alerting the care staff to perform timely pad/absorbent article changes reduces pad/absorbent article dermatitis/rash that can ultimately lead to skin issues. These alerts can be documented by time/date stamps that are automatically logged into a web portal that is managed by the healthcare facility or personal caregiver with the intention of providing statistical data as to when an event occurred and how long that patient was exposed to the insult before they receive attention.

SUMMARY OF THE INVENTION

The present invention relates to a signaling device configured to detect the presence of moisture in the absorbent article and/or in an undergarment. The signaling device can further wirelessly and/or visually provide notification to a nursing station and/or caregiver that an insult has occurred, thereby speeding up the response time for patient care. The signaling device can be imbedded or sewn into the absorbent article, or it can be removably affixed to the absorbent article.

BRIEF DESCRIPTION OF THE FIGURES

A full and enabling disclosure of the present invention, including the best mode thereof to one skilled in the art, is set forth more particularly in the remainder of the specification, including reference to the accompanying figures, in which.

DETAILED DESCRIPTION OF THE INVENTION

Figure 1:
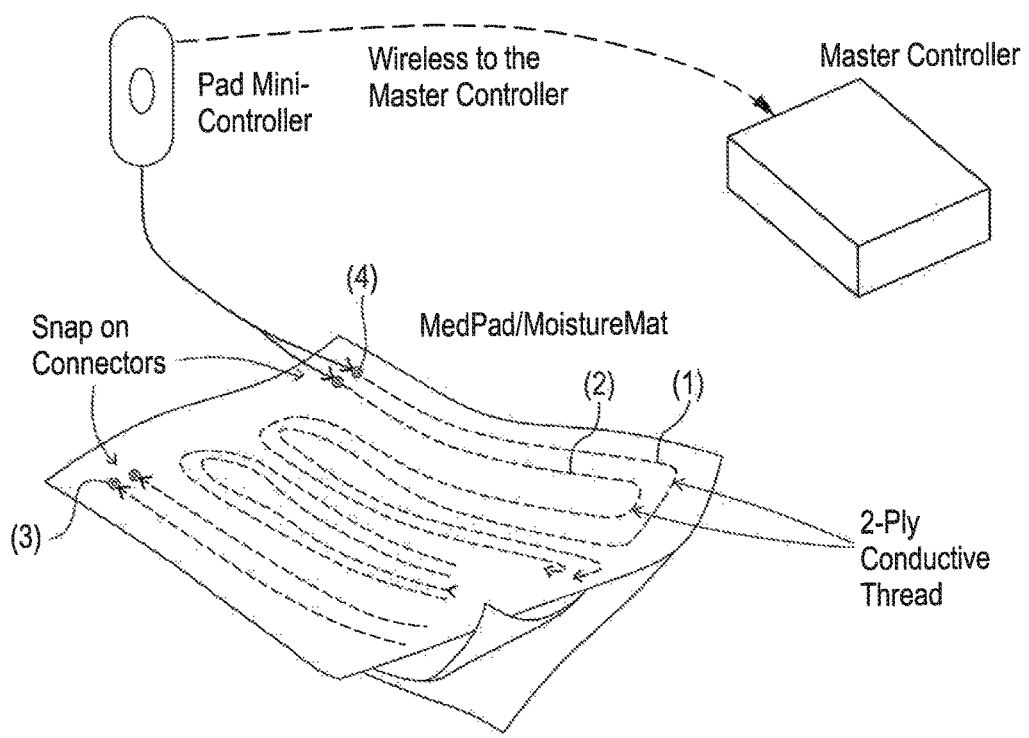
FIG. 1 is a perspective view of one embodiment of an absorbent article of the invention showing one possible sensor configuration.
Figure 2:
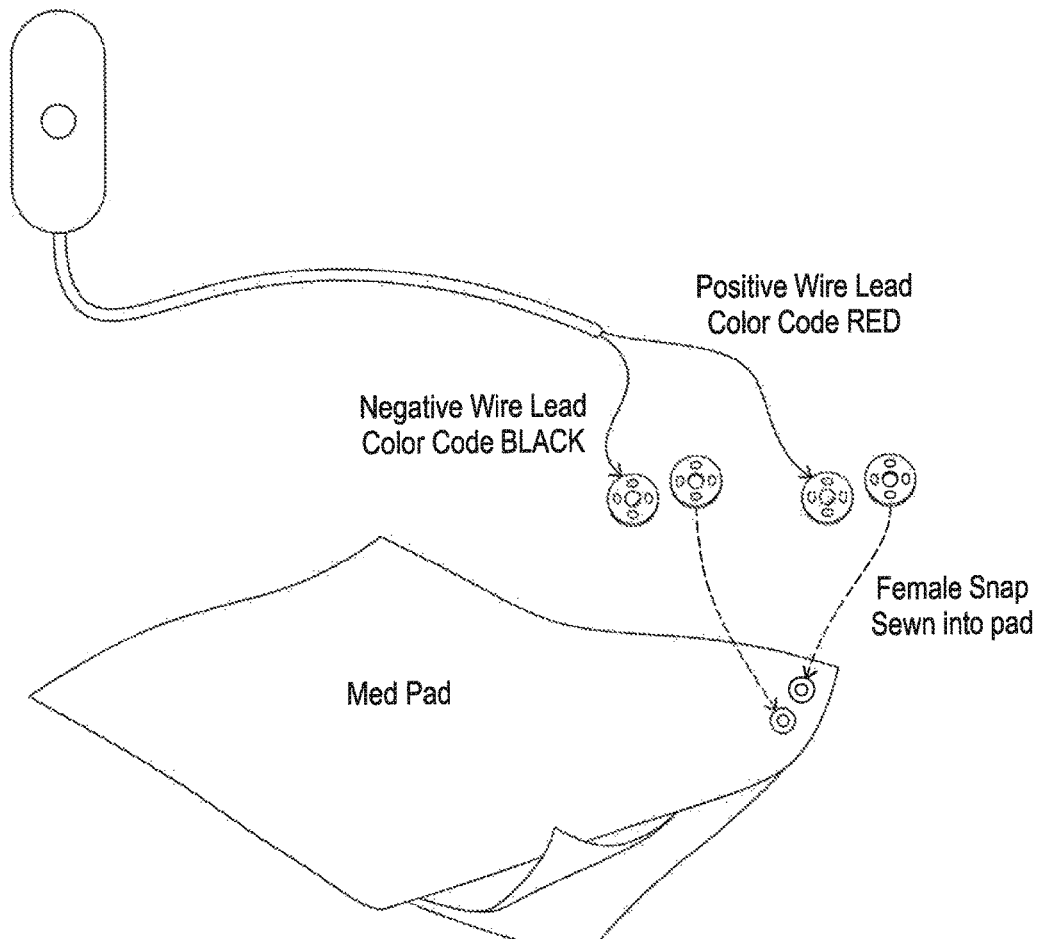
FIG. 2 is a front perspective view of the absorbent article according to an exemplary embodiment of the present disclosure.

The present invention generally provides a signaling device based on electrical detection using conductive elements separated by a distance on a substrate. In one embodiment, said substrate is on, within, is affixed to and/or comprises an absorbent article. These conductive elements are essentially wetness indicators that detect a change in an electrical property, such as impedance, due to the presence of an ionic liquid such as urine. The change in the electrical property triggers a signal or alarm to indicate the presence of wetness in the absorbent article.

In one embodiment, the invention relates to a signaling device for detecting an insult in an absorbent article. The signaling device includes a sensor configured to provide an output signal associated with an electrical property of the absorbent article. The electrical property changes in response to an insult. The signaling device further includes an electronic circuit coupled to the sensor.

In another embodiment, the signaling device is imbedded or sewn into the absorbent article.

In another embodiment, the signaling device is removably affixed to the absorbent article.

In yet another embodiment, the invention is directed to a method for detecting and identifying an insult in an absorbent article. The method includes monitoring an electrical property associated with the absorbent article, which changes in response to an insult. The method further includes detecting a change in the electrical property to determine the presence of an insult; and notifying the care giver in a timely automated manner to reduce response time, and ultimately reduce the probability of ulcers, dermatitis, rash and other skin issues.

The signaling device of the invention is configured to detect the presence of bodily fluids in an absorbent article or in an undergarment, and to inform the care giver that an insult has occurred. The signaling device of the invention can emit an audible and/or a visual signal in order to indicate to the user that the signaling device has detected an insult. The audible signal, for instance, may be as simple as one or more beeps. Similarly, if the signaling device issues a visible signal, the visible signal may comprise a few lights or an interactive display. In still another embodiment, the signaling device may be configured to vibrate when the circuit within the absorbent article is closed. In some embodiments, the signaling device can use a selected combination or all of the signaling techniques including, but not limited to vibration, visible signals, audio signals, and communication with remote devices, such as a smart phone or an IP based network. The signaling device can further wirelessly provide notification to a nursing station and/or caregiver that an insult has occurred, thereby speeding up the response time for patient care.

Discussion of an exemplary embodiment of the invention will be made with reference to FIG. 1. While the discussion of this embodiment is made with reference to a bed pad, it is understood that the present disclosure is suitable for use with various other absorbent articles.

FIG. 1 is an illustration of the signaling device of the invention in the form of a bed pad. The bed pad can be constructed in various ways as are known in the art, but typically they contain two or more layers, including a top layer, a middle absorbent layer and/or a moisture bather layer. The top layer typically does not substantially absorb moisture and allows moisture to pass to the middle absorbent layer. The moisture barrier layer prevents moisture from passing to, for example, the mattress. The bed pad can be designed and constructed to be reusable, or disposable. In FIG. 1, the middle layer of said bed pad is stitched a first conductive element (1) spaced from a second conductive element (2) in a substantially parallel manner approximately ½ into to 1 inch apart starting at one corner of the pad where two metal cleats (3) are located and continuing back to the opposite corner of the pad making a 180 degree turn and continuing back to the opposite end of the pad.

As one of ordinary skill will understand, the conductive elements (1) and (2) can extend any length of the bed pad as desired and they can be in any configuration suitable suitable to generate a signal in the presence of moisture. The conductive elements (1) and (2) can comprise any suitable conductive material, such as a conductive thread, printed conductive lines, conductive wires, conductive foil, and the like. The first conductive element (1) does not intersect the second conductive element (2) in order to form an open circuit that may be closed, for instance, when a conductive fluid or material, such as a urine insult or a feces insult, is positioned between the conductive elements. The end of each conductive element at the edge of the pad and is secured to two metal connectors or metal cleats (3) so that the pad can be tested by the care giver before each use. For testing, the care giver simply bridges the two cleats together with, for example, metal or a damp cloth when the pad is connected to a monitoring device. If the monitoring device flashes red, the pad is functional and ready for use. The distance between threads and the manner that they are stitched to said middle layer are non-limiting, and one of ordinary skill will recognize that the main importance is that a significant portion of said pad is traversed by said conductive thread. The distance between the conductive elements can, however, be varied in order to adjust moisture sensitivity.

Conductive elements (1) and (2) may be incorporated into the bed pad at any suitable location as long as the conductive elements are positioned so as to contact a body fluid that is exuded by a user. In this regard, the conductive elements (1) and (2) preferably lie inside the outer cover and above the absorbent layer of the bed pad.

The layers of the bed pad can be sewn together with conventional threads in standard patterns. It is important, however, that the bed pad layers be configured and sewn so that the two conductive threads do not contact each other when the pad is wrinkled and/or folded. In this regard, the middle absorbent layer can actually comprise two or more separate absorbent layers, each comprising conductive elements 1 and 2 respectively, such that said conductive elements are separated and do not contact each other. The distance between the conductive threads or elements and the absorbing layer thickness influences the response time to an insult.

At the starting point of said bed pad, the conductive element are secured to two metal connectors or cleats (3) thus providing a conductive platform. The cleats are configured to allow attachment of a snap, clamp like or other attachment means. In one embodiment, this attachment means is a clamp-like device which can communicatively attach to the cleats on said bed pad. To this clamp will be attached a circuit board or controller that will capture data and relay same through either wired or wireless means, back to the caregiver for quick response. Alternatively, this circuit board or controller can be imbedded within or is a part of said clamp. The clamp can also optionally comprise an LED light or other visual notification means that will flash when the pad is wet and the circuit will also pass this alert, along with a time and date stamp when the event took place to the care giver. The circuit within the clamp can also optionally have the ability to recognize the room and/or patient that it is monitoring. The clamp and associated circuit can be powered by simple battery, i.e., for example, a AA or AAA size battery, or by standard 110 AC power cord.

The signaling device of the invention comprises a water sensing mechanism formed by said first (1) and second conductive elements (2). As moisture or urine passes through the top layer of the bed pad, it soaks the middle absorbent layer. The urine conducts electric current between conductive element 1 and conductive element 2 completing the circuit and causing the alarm signal. This alarm signal can be configured to a microprocessor which can notify a user/nurses station of where water is present. Ideally this microprocessor can be configured to a master controller which can receive signals from multiple bed pads.

The bed pad (1) can be disposable or not. The bed pad can be fabricated to survive several wash cycles and normal wear and tear associated with typical use. Once completely dry, the bed pad will be able to be put back into use with the same monitoring accuracies.

The signaling device can be a separate article that is placed on or affixed to said bed pad by adhesive means, for example, by adhesive backing, double sided tape, Velcro fastening and the like. In this embodiment, a felt pad or other suitable textile material of construction is stitched in a manner similar to the way the middle layer is stitched in the bed pad. The article can be of varied shape, e.g., circular, square, rectangular, and the like. More specifically, the two conductive elements (1) and (2) can be two ply conductive thread or other conductive material sewn in a substantially parallel manner approximately ½ into to 1 inch apart starting at one corner of the pad where two metal cleats (3) are located and continuing back to the opposite corner of the article making a 180 degree turn and continuing back to the opposite end of the article. The end of each thread ends at the edge of the article and is secured to two metal cleats (4) so that the article can be tested by the care giver before each use. In this embodiment, the signaling device/article can have an adhesive backing that can be easily and quickly affixed to a conventional bed pad and/or absorbent article.

While the discussion of the exemplary embodiment are made with reference to a bed pad, it is understood that the present disclosure is suitable for use with various other absorbent articles intended for personal use and/or wear, including but not limited to diapers, training pants, swim pants, feminine hygiene products, incontinence products, medical garments, surgical pads and bandages, other personal care or health care garments, and the like without departing from the scope of the present disclosure. It should also be understood the various exemplary embodiments could also be used to identify and classify an insult in an undergarment if a user would like to monitor the presence of an insult without necessarily requiring an absorbent article.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged in whole, or in part. Furthermore, those of ordinary skill in the art will appreciate that the foregoing description is by way of example only, and is not intended to limit the invention so further described in such appended claims.

What is claimed is:

1. A bed pad with a body fluid sensor comprising:
   a first absorbent layer;
   a second absorbent layer;
   wherein the first absorbent layer further comprises a first conductive thread having a first length and a first metal attachment means on a first end of said first conductive thread;
   wherein the second absorbent layer further comprises a second conductive thread having a second length and a second metal attachment means on a first end of said second conductive thread;
   wherein the first conductive thread and the second conductive thread are disposed on the first and second layers respectively such that said first and second conductive threads do not contact each other thereby forming an open circuit;
   wherein the first and second metal attachment means provide a conductive platform configured to allow power to be supplied to the open circuit through the attachment means;
   wherein the first and second conductive threads form an open circuit under dry conditions, and wherein said open circuit is completed in the presence of a moisture insult causing an alarm signal indicating the presence of said insult.

2. The bed pad of claim 1, wherein said pad has an adhesive backing.

3. The bed sensor pad of claim 1, wherein the alarm signal is transmitted to a caregiver or nursing station.

4. The bed pad of claim 1, further comprising a moisture barrier layer.

5. The bed pad of claim 1, wherein the layers of said pad are configured and sewn such that said first and second conductive threads to not contact each other when said pad is wrinkled or folded.

6. The bed pad of claim 1, wherein said alarm signal is a visual or audible signal.

7. The bed pad of claim 4, wherein said alarm signal is transmitted to a remote device.

8. The bed pad of claim 7 wherein the remote device is a smartphone or an IP based network.

9. The bed pad of claim 1 wherein the circuit is powered by battery or AC power source.

* * * * *